(12) United States Patent
Bidoia et al.

(10) Patent No.: US 6,706,057 B1
(45) Date of Patent: Mar. 16, 2004

(54) COMPRESSION SUTURE DEVICE

(76) Inventors: Gianfranco Bidoia, Via Bressanone, 3/a, 35142 Padova (IT); Riccardo Annibali, Via Gran Paradiso, 5/b, 20020 Arese (IT)

( * ) Notice: Subject to any disclaimer, the term of this patent is extended or adjusted under 35 U.S.C. 154(b) by 189 days.

(21) Appl. No.: 09/713,294

(22) Filed: Nov. 16, 2000

(30) Foreign Application Priority Data

Nov. 18, 1999 (IT) .......................................... PD99A0256

(51) Int. Cl.[7] .............................................. A61B 17/08
(52) U.S. Cl. ...................................... 606/220; 606/139
(58) Field of Search ................................. 606/219, 220, 606/139, 238, 142, 140, 143; 227/175.1

(56) References Cited

U.S. PATENT DOCUMENTS 5,662,259 A * 9/1997 Yoon ........................ 227/176.1

* cited by examiner

*Primary Examiner*—John J. Calvert
*Assistant Examiner*—James G Smith
(74) *Attorney, Agent, or Firm*—Guido Modiano; Albert Josif; Daniel O'Byrne

(57) ABSTRACT

A compression suture device for the surgical treatment of hemorrhoids, comprising two mutually opposite sections, each of which has a portion for mutual irreversible connection and a clamping portion for at least two flaps of organic tissue which are arranged in contact.

5 Claims, 7 Drawing Sheets

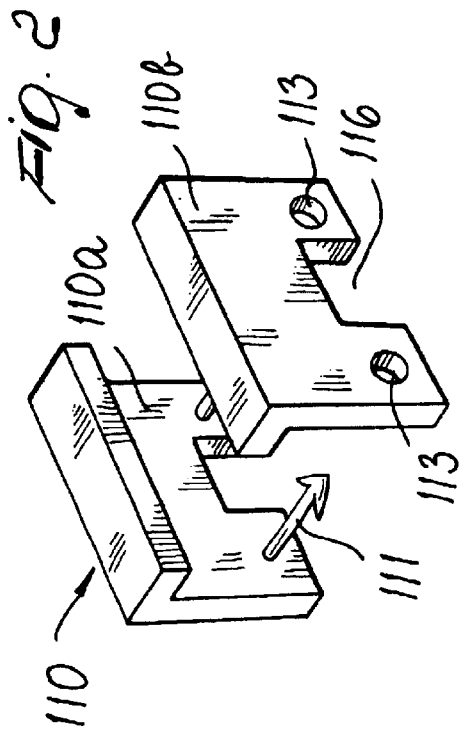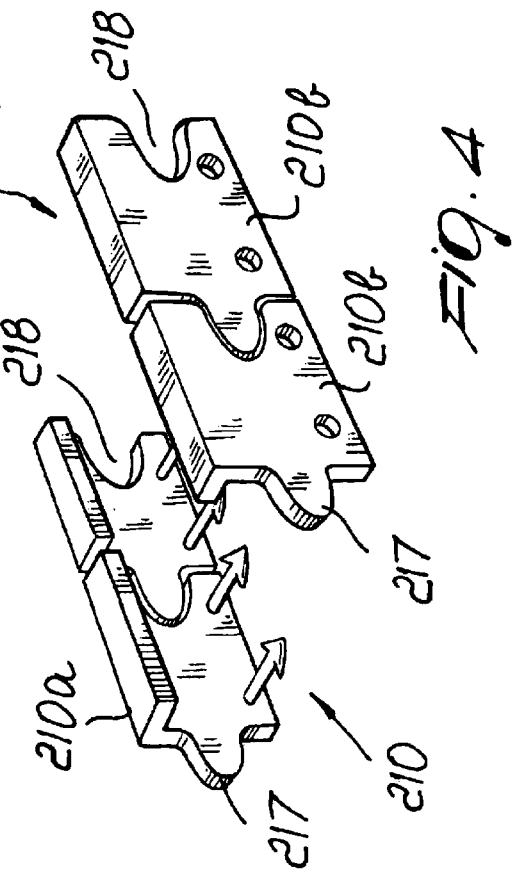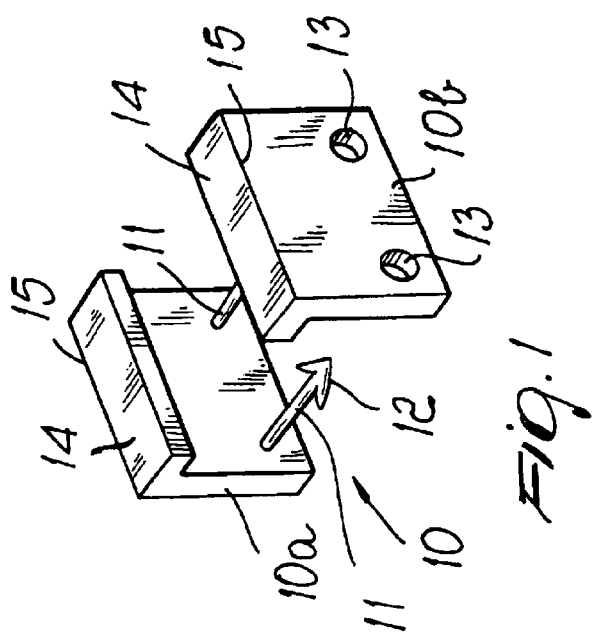

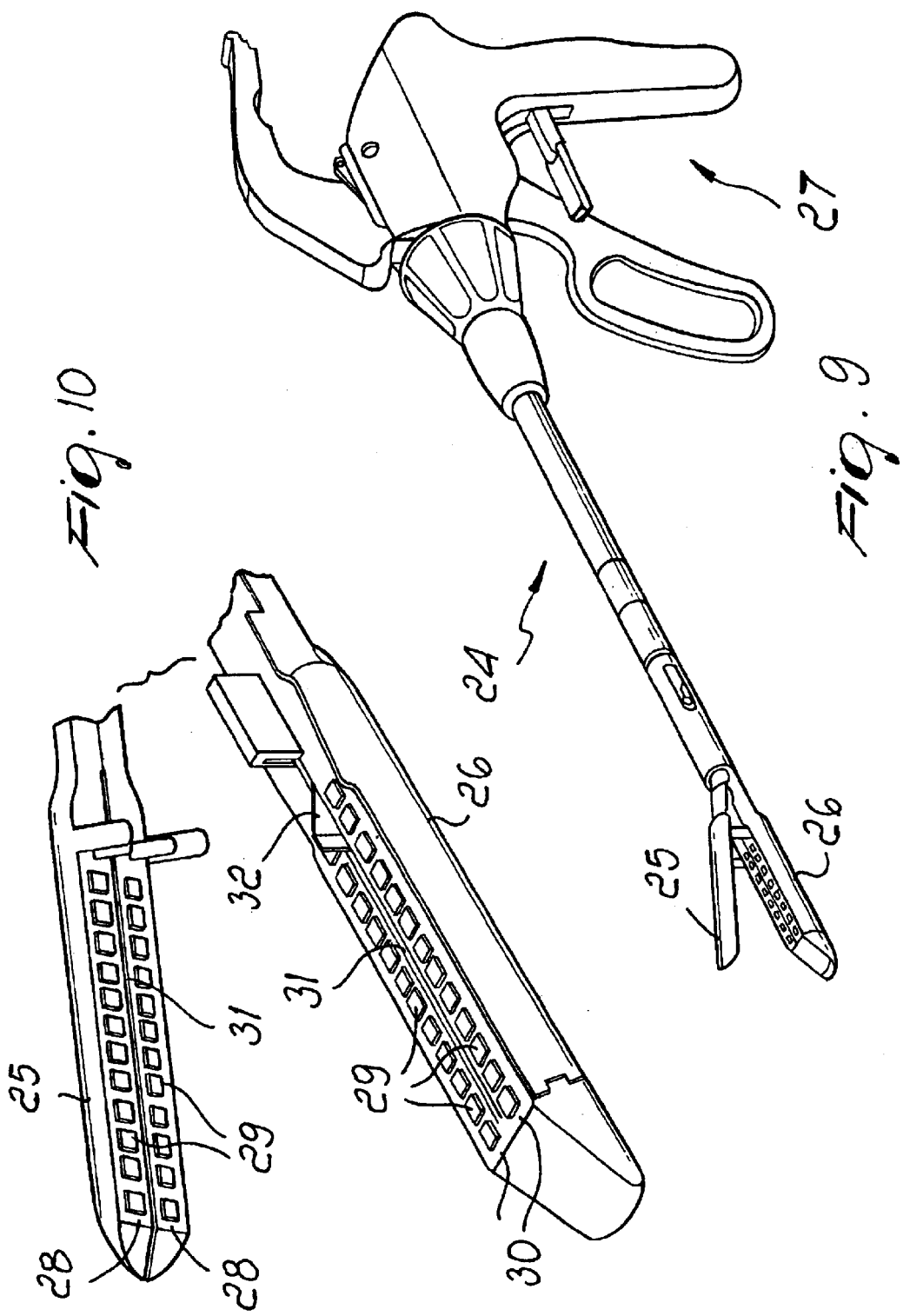

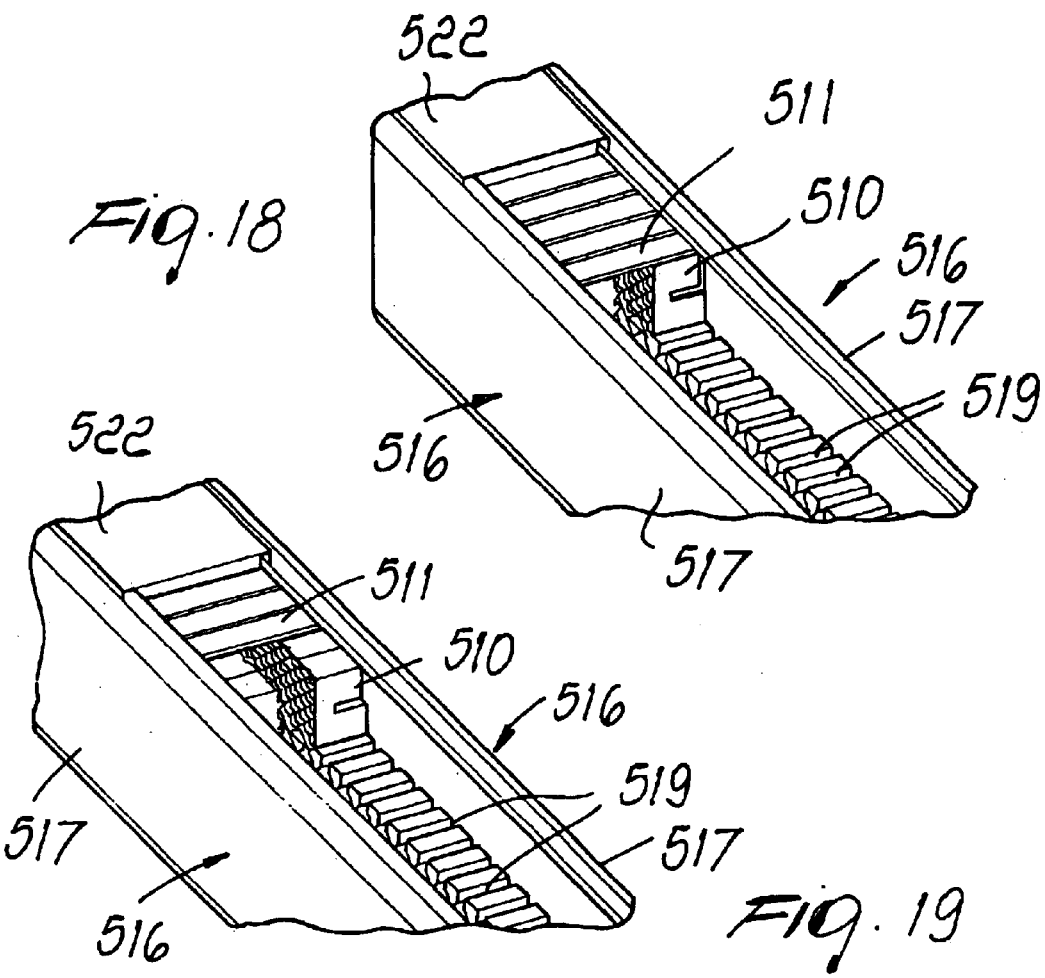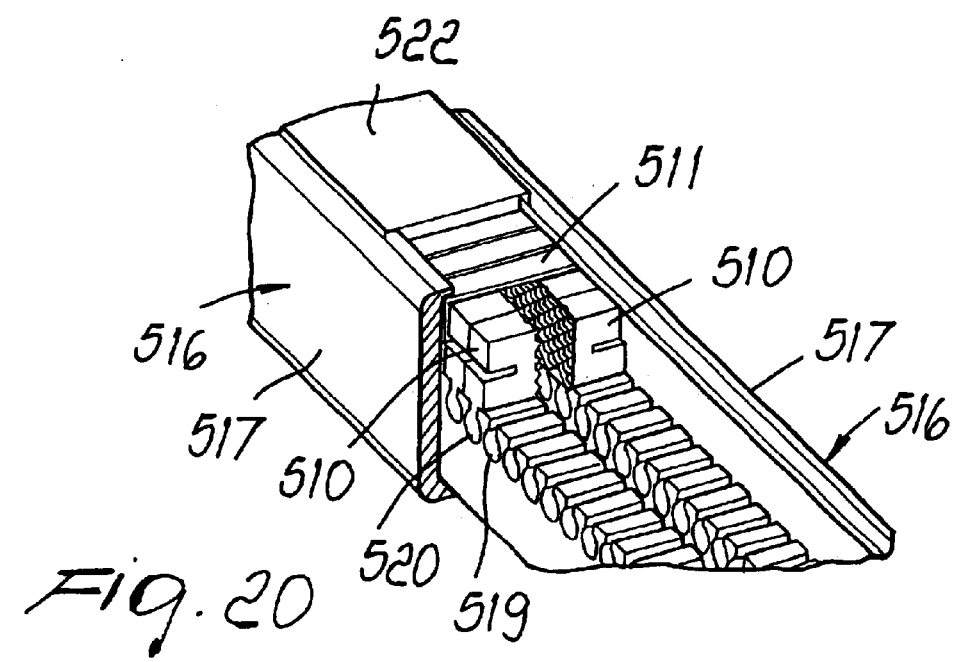

COMPRESSION SUTURE DEVICE

BACKGROUND OF THE INVENTION

The present invention relates to a compression suture device.

The device is particularly but not exclusively suitable for the surgical treatment of hemorrhoids.

Various techniques for the surgical treatment of hemorrhoids are available.

The two currently most widely known and used methods are the open technique (used mainly in Europe) and the closed technique (used mainly in the American continent).

The closed technique has considerable advantages in terms of painful complications and speed of healing with respect to the open technique, although it requires greater training of the surgeon and is more expensive.

These techniques have always been performed with reusable surgical instruments and the stitches have been applied with the classic needle-and-thread method.

During the second half of this century, various surgical instruments known as surgical staplers have been provided in order to facilitate the execution of linear or circular sutures, making them faster and safer even in areas and conditions in which the classical manual suture entails difficulties.

These instruments can be of the throwaway type or not, perform linear or circumferential sutures, and act by applying a plurality of staples which are very similar to the typical metallic staples of an ordinary office stapler.

Since these staples are usually permanent, titanium has been used preferentially as a material, in view of the known characteristics of biocompatibility, strength, light weight, and elasticity of this material.

There are also other suture systems, which however utilize the capacity of biological tissues to heal when they are kept joined with a certain pressure and for a certain period of time.

This last type of suture is commonly known as compression suture.

Compression sutures are used for the synthesis of hollow viscera after the surgical removal of a segment and for surface tissues (skin and mucous membranes) and are performed by means of bandages or adhesive bands, elastic rings made of latex or silicone.

The considerable advantage of compression suture systems is that once their task has been completed they can be removed or they can fall spontaneously and be subsequently eliminated from the body.

Substantially, these are "continuous" systems, such as an elastic element, a synthetic thread or a body, with a possibly nonstandard geometric shape, and they cannot be applied in the case of a long and longitudinal suture, especially if it is enclosed in a small cavity.

As regards hemorrhoids, circular staplers designed and manufactured specifically for this purpose have recently been used.

This technique allows to rapidly perform the suture inside the anal canal, above the dentate line and therefore in a region where pain sensitivity is very limited.

Actually, this is not a true hemorrhoidectomy but rather a correction of the hemorrhoidal prolapse which is often associated with hemorrhoids.

Adequate and complete treatment of hemorrhoids must entail a "radical hemorrhoidectomy", i.e., the complete removal of the hemorrhoidal columns in order to prevent relapses which can occur starting from the abnormal swelling of the residual hemorrhoidal tissue.

Moreover, complete treatment of hemorrhoids entails removal of the external hemorrhoidal bundles, in order to prevent any future disorder linked to alteration of these structures.

The known techniques for the treatment and healing of hemorrhoids are not free from drawbacks.

Hemorrhoidectomy with a circular stapler "suspends" the hemorrhoidal tissue in the anal canal but does not remove it completely: approximately the lower half of the internal hemorrhoids and all of the external hemorrhoids are in fact left in place.

There is a certain incidence of external hemorrhoidal thromboses and thrombophlebitides in the immediate postoperative period which eliminates the potential benefits of the use of the stapler.

Various degrees of postoperative anal stenosis have been observed after the use of a circular stapler for hemorrhoids.

It is necessary to wait longer to reveal any relapses arising from the residual internal hemorrhoids.

Although made of an inert material (titanium), the staples used for the suture cannot be eliminated, and this entails, for the patients, psychological unease in accepting foreign material permanently in their body as well as physical discomfort, such as small losses of blood when the friction of bulky stools causes the separation of a few staples even long after the operation.

Moreover, a single element compressing the hemorrhoidal tissue along its entire length would produce an excessively rigid suture, since the columns to be removed for radical hemorrhoidectomy are generally three, one in the left quadrant and two in the right quadrant, front and rear, the combination of three rigid elements would cause excessive overall rigidity in the anal canal and might compromise defecation.

Finally, the cost of the procedure is particularly high and linked to the cost of the throwaway stapler that is used.

SUMMARY OF THE INVENTION

The aim of the present invention is to provide compression suture devices which allow to provide an effective hemorrhoidectomy with the closed technique.

A consequent object is to join the tissue without permanent stitches.

Another object is to achieve return of the tissue to total elasticity.

Another object is to avoid patient blood losses or in any case drastically reduce their extent.

Another object is complete and radical removal of the hemorrhoidal columns.

Another object is to eliminate the problem of hemorrhoids, with the possibility to correct any concurrent occult mucous membrane rectal prolapse.

Another object is to provide compression suture devices which are adapted to be used in straight, curved and circular shapes on organic tissues that have already been moved mutually close by other instruments and are to be kept joined and compressed together in order to be sutured and/or connected permanently.

Another object is to provide compression suture devices which are eliminated spontaneously and without the need for human and/or mechanical intervention.

Another object is to provide compression suture devices which are applied by means of applicators having different apertures, thicknesses, dimensions and shapes so as to be used in any situation or physiological region, hemorrhoids not being a requirement.

Another object is to provide compression suture devices which can be arranged on a same plane and/or on different planes, whether parallel or staggered or consecutive.

Another object is to provide compression suture devices which can also coexist with devices having different shapes, materials and dimensions, on the same line and on different planes.

Another object is to provide a compression suture which can also include or not (simultaneously, before or after application) the possibility to perform incision, cutting, elimination, cauterization and/or coagulation of the organic tissue, optionally obtained by means of high-frequency applications or the like, in combination with each other or not, and which allows this possibility to be included and/or provided by the applicator itself or not.

Another object is to provide a suture which can also be applied to other surgical procedures which entail the need to join and compress organic tissues and to allow subsequent elimination of the suture devices through natural and/or physiological pathways.

Another object of the invention is to maintain all the advantages of the closed technique in hemorrhoid treatment, making it easier and faster to perform and within the grasp of any surgeon even if he is not expert in the field of proctology.

Another object is to maintain relatively low costs.

This aim and these and other objects which will become better apparent hereinafter are achieved by a compression suture device, comprising two mutually opposite sections which cooperate with mutual connection means and a clamping portion for at least two flaps of organic tissue placed in mutual contact.

BRIEF DESCRIPTION OF THE DRAWINGS

Further characteristics and advantages of the invention will become better apparent from the detailed description of an embodiment thereof, illustrated only by way of non-limitative example in the accompanying drawings, wherein:

FIG. 1 is a perspective view of a first embodiment of a device according to the invention;

FIG. 2 is a perspective view of a second embodiment of a device according to the invention;

FIG. 3 is a side view of the devices shown in the preceding figures;

FIG. 4 is a perspective view of a third embodiment of a device according to the invention;

FIG. 9 is a perspective view of an applicator according to the invention;

FIG. 10 is an enlarged-scale perspective view of a detail of the applicator of FIG. 9;

FIGS. 15 to 20 are enlarged-scale perspective views of details of a second embodiment of an applicator for the device in its sixth embodiment.

DESCRIPTION OF THE PREFERRED EMBODIMENTS

Figure 5:
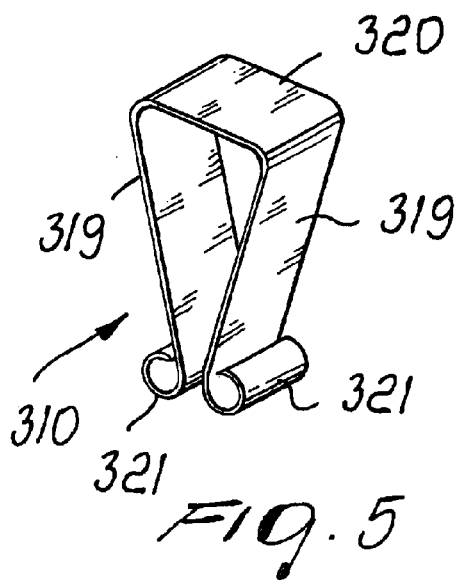
FIG. 5 is a perspective view of a fourth embodiment of a device according to the invention.
Figure 6:
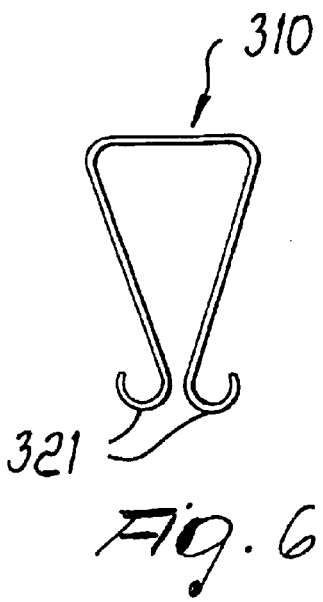
FIG. 6 is a side view of the device of FIG. 5.

With reference to FIG. 1, a device according to the invention is designated by the reference numeral 10.

The device 10 is constituted by two plate-like elements 10a and 10b which are provided with means for irreversible mutual connection and comprise two spaced longitudinally elongated elements 11 which are arranged at right angles and rigidly coupled to the element 10a and are provided with an arrow-shaped head 12 for irreversible insertion in corresponding holes 13 formed in the corresponding element 10b.

The elements 10a and 10b are further provided with clamping portions which are constituted by wings 14 arranged at 90 sexagesimal degrees along a longitudinal plane 15, said wings 14 being arranged so as to face each other.

A second embodiment of the invention is shown in FIG. 2.

The only difference between this embodiment 110 and the preceding one 10 is that the plate-like elements 110a and 110b have recesses 116 between the longitudinally elongated elements 111 and between the holes 113.

A third embodiment of the invention is shown in FIG. 4.

The device 210 comprises, along its longitudinal extension, for each element 210a and 210b, a protrusion 217 with a rounded head on one side and a complementarily shaped recess 218 on the other side, so as to provide locators for identical devices 210 arranged longitudinally adjacent to each other.

In this manner it is possible to obtain a continuous but not rigid suture line.

A fourth embodiment of the invention is shown in FIG. 5.

The device 310 is constituted by two plate-like elements 319 which are monolithic with an element 320 arranged substantially at right angles to the elements 319, forming two elastic wings.

The ends 321 of the elements 319 are folded, and such ends 321 clamp the two flaps of biological tissue to be sutured, which are not shown in the figure.

Figure 7:
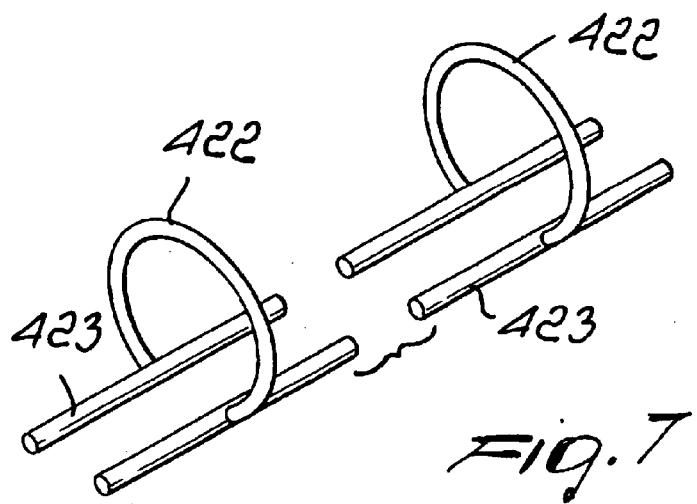
FIG. 7 is a perspective view of a fifth embodiment of a device according to the invention.
Figure 8:
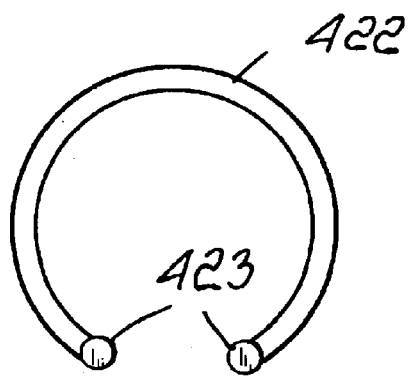
FIG. 8 is a side view of the device of FIG. 7.
Figure 11:
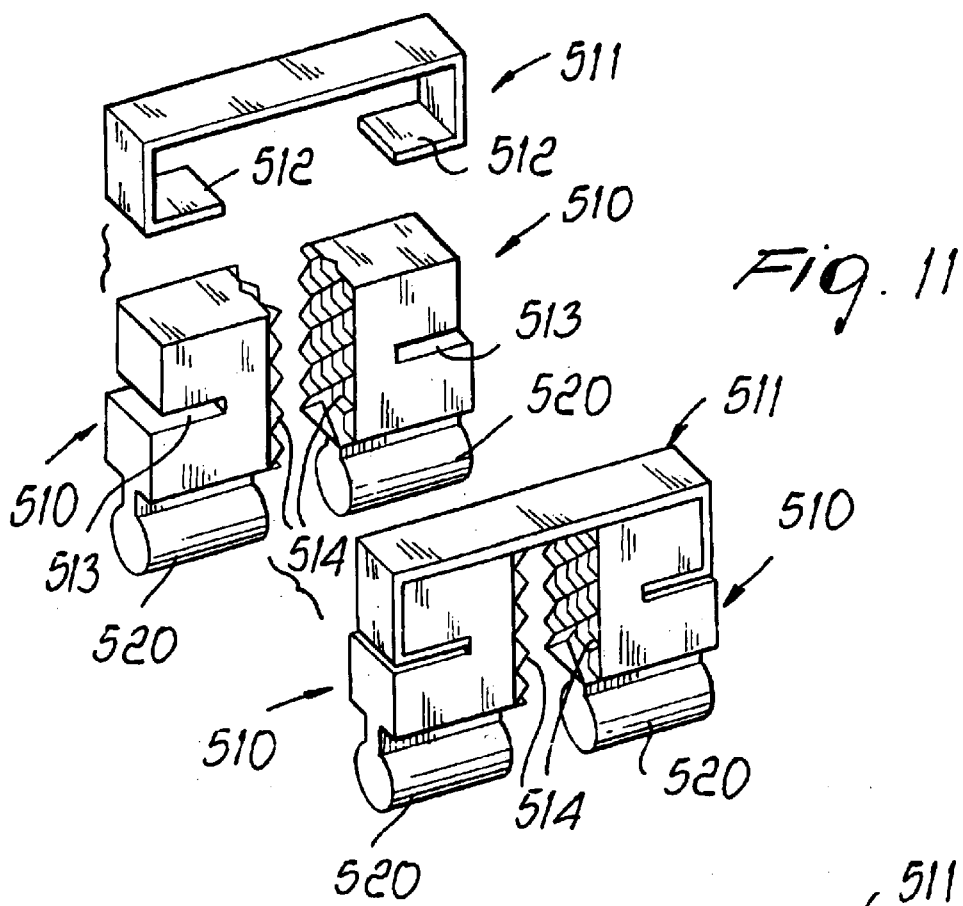
FIGS. 11 to 14 are various views of a sixth embodiment of the device according to the invention.
Figure 12:
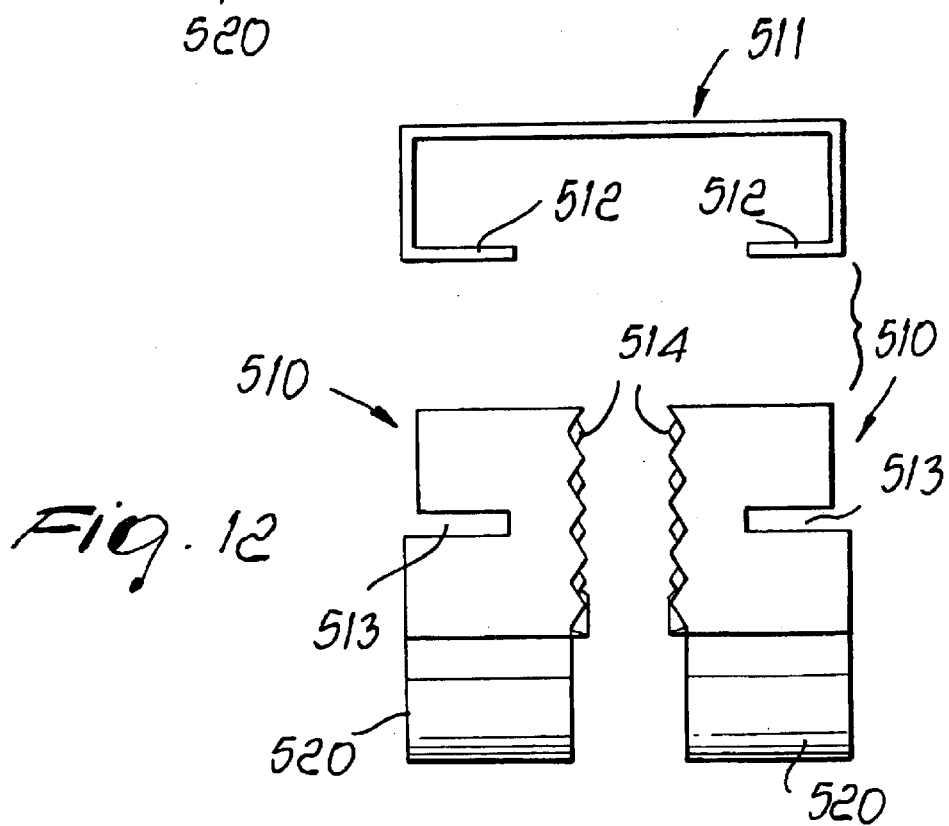
Figure 13:
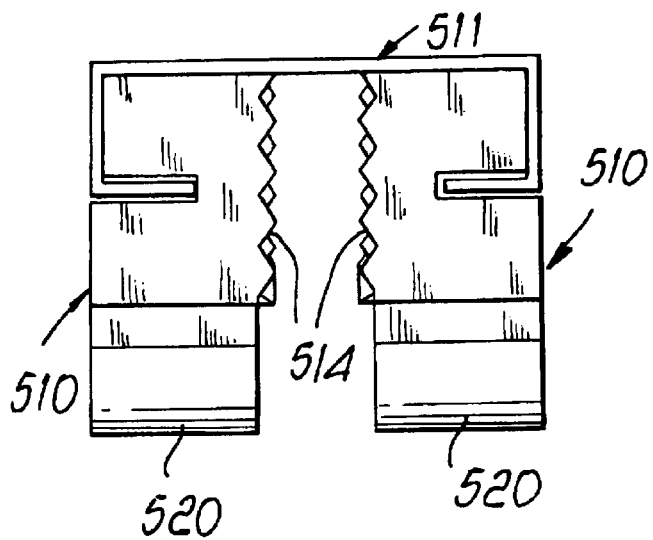
Figure 14:
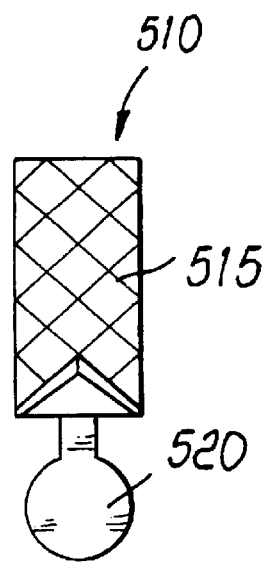
Figure 17:
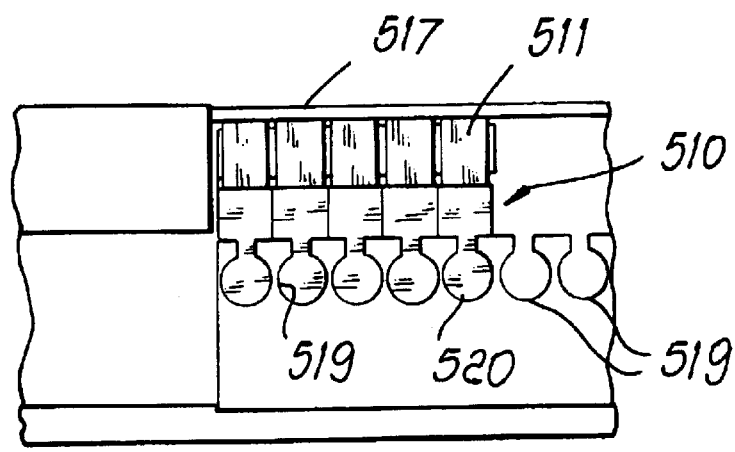
Figure 15:
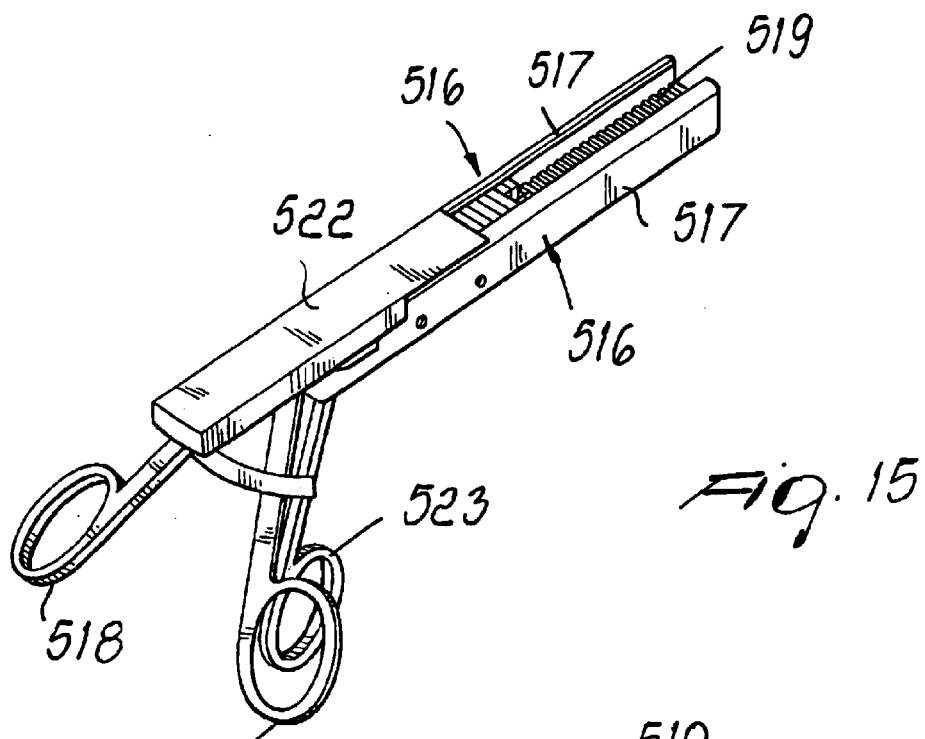
Figure 16:
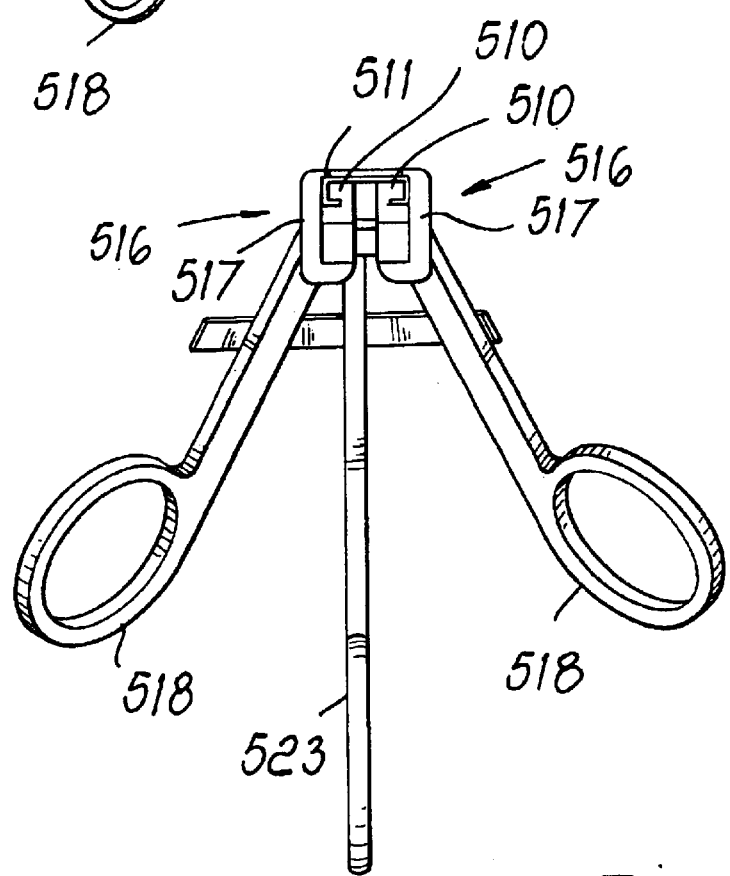

A fifth embodiment of the invention, which like the preceding device 320 elastically clamps the biological tissue to be sutured, is shown in FIG. 7.

The device 410 is constituted by an elastically deformable open ring 422 which has rod-like clamping elements 423 at its ends, which are arranged at right angles to its main plane.

Advantageously, for example the above-described devices can be between 4 and 10 mm high, their minimum width is 2 mm, their length is between 2 and 6 mm, and their mutual spacing is approximately 0.05/0.1 mm.

Owing to the particular use of these devices, they must be made of a material which is not only elastically deformable but also biocompatible.

An applicator for devices 10, 110 and 210 is designated by the reference numeral 24.

The applicator 24 comprises two pincer-like jaws 25 and 26 which are moved by manual controls 27: the jaw 25 is provided with two rows 28 of seats 29 for an element 10a/10b, 110a/110b or 210a/210b of the device 10, 110 or 210, and the other jaw 26 is provided with two corresponding rows 30 of seats 29 for their complementary part 10b/10a, 110b/110a, or 210b/210a.

A seat 31 for the sliding of a corresponding blade 32 used to cut the flaps of sutured tissue is provided between each pair of rows 28 and 30.

An applicator 24 can be provided with a single row of seats 29 and may not have the blade 32.

As regards operation, by utilizing the biological principle of natural and spontaneous joining of human tissues subjected to compression, one can obtain results in the treatment of hemorrhoids which respect physiology and the ability to regenerate of organic tissues.

The principle consists in "trapping" the hemorrhoidal column to be removed, which comprises both the external hemorrhoidal bundle and the internal one, between the jaws of the linear compression stapler 24: the tissue to be removed is removed by cutting it at the base along the line of the clamp of the stapler by means of the blade 32.

At this point it is necessary to perform the synthesis of the two portions of mucous membrane that have remained trapped and are in mutual contact within the clamp of the stapler 24.

This can be achieved by "loading" one of the two jaws, for example the jaw 25, with a plurality of plates, for example 10a, which join to the complementary part 10b, accommodated in the other jaw 26, with a simple interlocking system.

The aperture can have a variable size according to the thickness of the tissues to be sutured.

With particular reference to the above-cited FIGS. 11–14, in a sixth embodiment the device according to the invention is composed of two mutually identical plates 510 to be arranged in a mirror-symmetrical fashion with the flaps of tissue to be joined interposed between them, and by a transverse bridge-like connecting element 511 with edges 512 which are folded inward for insertion in corresponding longitudinal slots 513, one for each plate.

A surface 514 of each plate 510 to be arranged in contact with the tissue is appropriately knurled.

For these plates 510 it is possible to use an applicator 515 which comprises two supporting elements 516 which are mutually articulated in a scissor like configuration.

Each element 516 is composed of a straight portion 517 having a substantially C-shaped cross-section and by a shaped portion 518 with grip rings.

Each portion 517 is shaped, in the region that corresponds to the one that lies opposite the location of the connecting elements 511, so as to form a plurality of transverse seats 519 which are shaped complementarily to tabs 520 which protrude from the plates 521.

The tabs 520 (and, correspondingly, the seats 519) are enlarged at their ends in order to allow coupling and uncoupling only by mutual sliding.

Each portion 517, above the region for fixing said plates 510, is shaped so as to have, between the wings of the C-shaped cross-section, the space is for the translatory motion of the connecting elements 511 in succession with respect to each other by way of the action of a pusher 522 which is rigidly coupled between the supporting elements 516 and is provided with an annular grip portion 523.

The first connecting element 511 of each series used must have a sharp edge in order to provide a sort of trimming of the edges of the tissues to be joined.

In the latter case, operation is as follows: by means of the applicator 515 with open supporting elements 516, the plates 510 are inserted one by one, or simultaneously if mutual connections are provided, in the portions 517 of the supporting elements 516, particularly by inserting the tabs 520 in the seats 519.

The supporting elements 516 are then closed so as to enclose the flaps of tissue to be joined, which are not shown.

The next operation is the translatory motion of the connecting elements 511, by means of the pusher 522 which advances stepwise, until all the pairs of plates 510 are locked.

The final operation is the opening of the supporting elements 516 and the disengagement, by sliding, of the tabs 520 of the plates 510.

At this point it should be noted that this new system obtains a tissue suture line at its base because the portion of tissue that is compressed between the plates in the upper part undergoes necrosis, i.e., it dies and is eliminated.

The continuity of the mucous membrane and of the skin after complete removal of the hemorrhoidal column is achieved without actual "stitching" and is determined by the continuous compression provided by the consecutive series of these devices, which are similar to many small railroad cars.

Once this has occurred, these devices detach spontaneously together with the compressed tissue, leaving a line of scar tissue at the base.

The reason for which it is important that compression be performed by means of a continuous line of small mutually articulated elements is that a single element compressing the hemorrhoidal tissue along its entire length would produce an excessively rigid suture.

Since the columns to be removed for radical hemorrhoidectomy are generally three (one in the left quadrant and two in the right front and rear quadrant), a set of three rigid elements would cause excessive overall rigidity in the anal canal and might compromise defecation.

Accordingly, it becomes indispensable to arrange an entire consecutive but separate series of elements that maintain compression and are eliminated as their action achieves the joining and healing of the tissues on which they have been arranged.

In practice it has been observed that the intended aim and objects of the present invention have been achieved.

The invention thus conceived is susceptible of numerous modifications and variations, all of which are within the scope of the inventive concept.

All the details may further be replaced with other technically equivalent elements.

In practice, the materials employed, so long as they are compatible with the contingent use, as well as the dimensions, may be any according to requirements.

The disclosures in Italian Patent Application No. PD99A000256 from which this application claims priority are incorporated herein by reference.

What is claimed is:

1. An applicator with a plurality of compression suture devices, wherein said compression suture devices comprise:
   two mutually opposite plate sections (510);
   a mutual connecting element (511) for mutually connecting said two opposite plate sections (510);
   clamping portions (514) of said two opposite plate sections (510) for clamping at least two flaps of organic tissue arranged in mutual contact between said clamping portions (514); and
   tab portions (520) protruding from said two opposite plate sections (510);

and wherein said applicator comprising two supporting elements (516) which are mutually articulated in a scissorlike fashion such that said two supporting elements (516) may be mutually spaced apart in an open configuration and such that said two supporting elements (516) may be mutually closed into a closed configuration for enclosing said flaps of organic tissue to be joined, each element (516) being composed of a straight portion (517) which has a substantially C-shaped cross-section and by a shaped grip portion (518) for moving said elements between said open and closed configurations, each C-shaped straight portion (517) being shaped, in a first end region thereof, so as to form a series of transverse seats (519) which are shaped complementarily to said tab portions (520) and inside which said tab portions (520) are slidingly arranged and whereby said clamping portions (514) are arranged in a middle portion of said C-shaped straight portion (517) adjacent said fist end portion thereof, each C-shaped straight portion (517) being shaped, in a second end portion thereof arranged adjacent said middle portion opposite said first end portion, so as to have, between wings of the C-shaped straight portion (517), a space in which the connecting elements (511) are slidingly arranged for the translatory motion of the connecting elements (511) one after the other by way of action of a pusher (522) which is rigidly coupled between said supporting elements (516) and is provided with a grip portion (523) for actuation thereof.

2. An applicator in combination with compression suture devices for applying said compression suture devices to organic tissues by clamping and compression joining of at least two flaps of the organic tissues with said compression suture devices, the suture devices comprising each two mutually separate and opposite sections, connection elements for connecting said two mutually separate and opposite sections and respective clamping portions provided at said mutually separate and opposite sections for clamping the organic tissues so as to enable suture thereof by compression, the applicator comprising two supporting elements for supporting each a plurality of respective opposite sections of the suture devices, said supporting elements being articulated to each other so as to be movable in a scissorlike fashion between: an open configuration for arrangement of said respective opposite sections so as to be supported by said supporting elements and for subsequent application of the suture devices to the organic tissues by arranging said at least two flaps of the organic tissues between said supporting elements with said respective opposite sections supported thereby in said open configuration; and a closed configuration for applying compression to the organic tissues and for fixing said respective opposite sections with said connection elements.

3. The applicator in combination with compression suture devices according to claim 2, wherein said supporting elements comprise two pincer-like jaws, one jaw of said two pincer-like jaws having a row of seats for supporting first ones of said respective opposite sections of said suture devices, another jaw of said two pincer-like jaws having a corresponding row of seats for supporting second complementary ones of said respective opposite sections of said suture devices.

4. The applicator in combination with compression suture devices according to claim 3, wherein said jaws have two rows of said seats between which there is a seat for sliding of a blade for cutting said at least two flaps of the organic tissues.

5. A method for applying compression suture devices to organic tissues by clamping and compression joining of at least two flaps of the organic tissues with said compression suture devices, comprising the steps of:

providing an applicator in combination with compression suture devices wherein the suture devices comprising each two mutually separate and opposite sections, connection elements for connecting said two mutually separate and opposite sections and respective clamping portions provided at said mutually separate and opposite sections for clamping the organic tissues so as to enable suture thereof by compression, and wherein the applicator comprising two supporting elements for supporting each a plurality of respective opposite sections of the suture devices, said supporting elements being articulated to each other so as to be movable in a scissorlike fashion;

arranging said supporting elements in an open configuration arranging said respective opposite sections so as to be supported by said supporting elements;

applying the suture devices to the organic tissues by arranging said at least two flaps of the organic tissues between said supporting elements with said respective opposite sections supported thereby in said open configuration; and arranging said supporting elements in a closed configuration and thereby applying compression to the organic tissues; and fixing said respective opposite sections with said connection elements.

* * * * *